(12) United States Patent
Peters et al.

(10) Patent No.: US 7,534,995 B2
(45) Date of Patent: May 19, 2009

(54) DEVICE FOR EXAMINING ROTOR DRILLED HOLES

(75) Inventors: Stephan Peters, Oberhausen (DE); Sönke Rapp, Essen (DE); Eiko Räkers, Oer-Erkenschwick (DE)

(73) Assignee: Deutsche Montan Technologie GmbH, Essen (DE)

( * ) Notice: Subject to any disclaimer, the term of this patent is extended or adjusted under 35 U.S.C. 154(b) by 390 days.

(21) Appl. No.: 11/579,399

(22) PCT Filed: May 20, 2005

(86) PCT No.: PCT/EP2005/005474

§ 371 (c)(1),
(2), (4) Date: Nov. 2, 2006

(87) PCT Pub. No.: WO2005/116401

PCT Pub. Date: Dec. 8, 2005

(65) Prior Publication Data

US 2008/0283738 A1    Nov. 20, 2008

(30) Foreign Application Priority Data

May 28, 2004  (DE) ................. 10 2004 026 702

(51) Int. Cl.
*G01V 5/08*  (2006.01)
*G01N 21/00*  (2006.01)
*G06K 9/00*  (2006.01)

(52) U.S. Cl. .............. 250/269.1; 368/241.1; 368/241.5; 382/109

(58) Field of Classification Search .............. 250/269.1; 356/241.1, 241.5; 382/109
See application file for complete search history.

(56) References Cited

U.S. PATENT DOCUMENTS

| 4,899,277 A * | 2/1990 | Iizuka et al. ............... 702/6 |
| 2003/0117617 A1* | 6/2003 | Taylor et al. ............ 356/241.4 |
| 2008/0283738 A1 | 11/2008 | Peters et al. ............ 250/269.1 |

\* cited by examiner

*Primary Examiner*—David P Porta
*Assistant Examiner*—Mindy Vu
(74) *Attorney, Agent, or Firm*—Andrew Wilford

(57) ABSTRACT

A probe for inspecting an anchor borehole has a video head provided with a color CCD sensor, a lens, a conical viewing window, and light-emitting diode for illuminating and optically scanning a borehole surface. The probe also has a travel sensor, an electronics module including two position sensors, a memory module, and a battery section carrying an infrared interface. The probe is cableless and autarchic. The battery section is secured to a leading end of a push rod.

5 Claims, 5 Drawing Sheets

DEVICE FOR EXAMINING ROTOR DRILLED HOLES

CROSS REFERENCE TO RELATED APPLICATIONS

This application is the US national phase of PCT application PCT/EP2005/005474, filed 20 May 2005, published 08 Dec. 2005 as WO2005/116401, and claiming the priority of German patent application 102004026702.2 itself filed 28 May 2004, whose entire disclosures are herewith incorporated by reference.

FIELD OF THE INVENTION

The invention relates to an apparatus for inspecting anchor boreholes and comprises a probe that has an optical acquisition device and that can be moved in the borehole with a pipe string.

BRIEF DESCRIPTION OF THE DRAWING

U.S. Pat. No. 5,663,559 describes a method and an apparatus for producing an image of an earth formation in oil-prospecting bores.

EP 0658 253 B1 discloses a borehole observation instrument for inspecting the interior of a borehole or shaft in oil prospecting bores.

Figure 1:
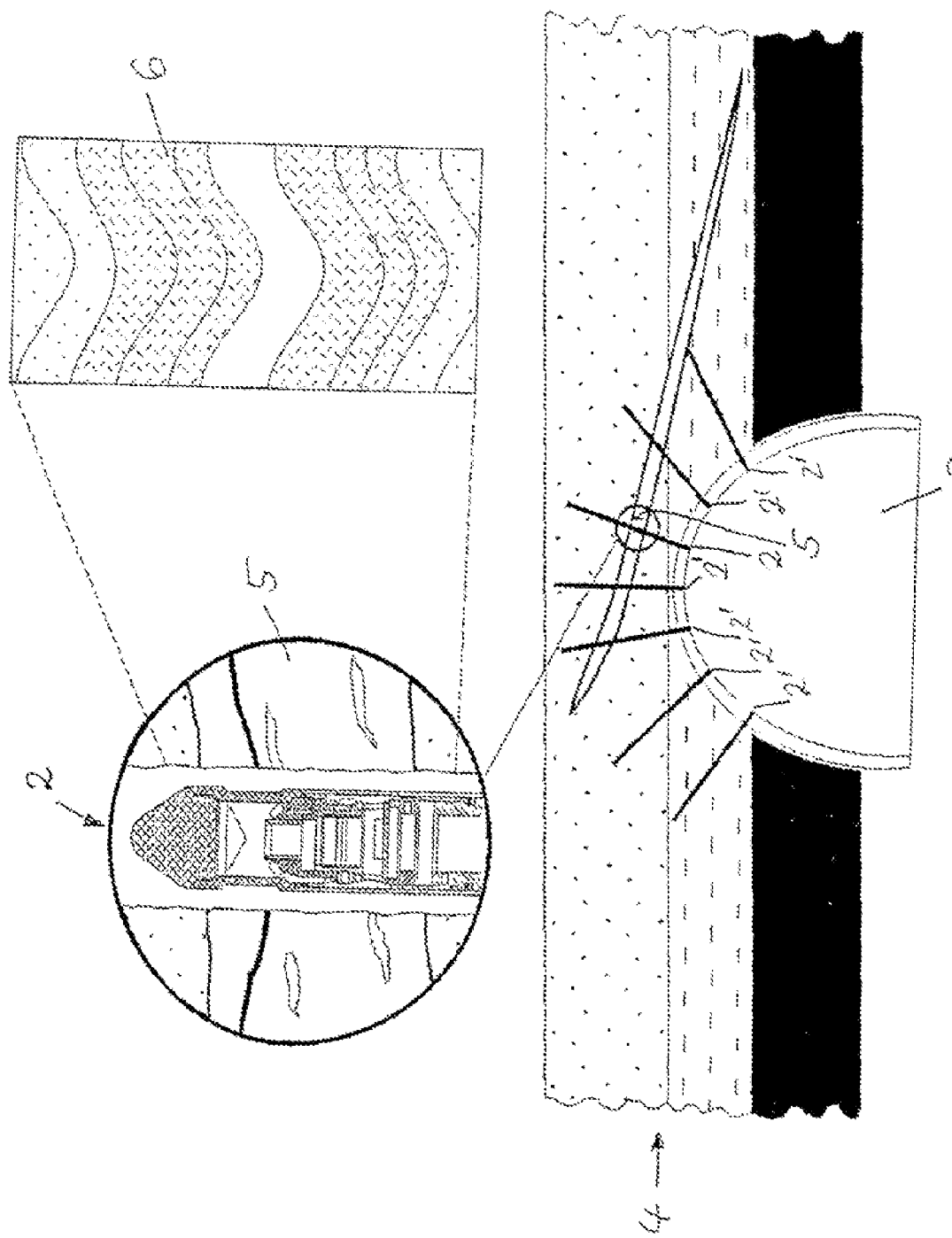

WO 94/07147 A1 relates to a method of and an apparatus for simultaneous video-technical determination of the flow direction and speed of groundwater for bore diameters >2 inches.

The methods and apparatuses disclosed in these publications are not suitable for inspecting anchor boreholes because anchor boreholes generally have a diameter of 1 to 2 inches.

It is known from DE 199 25 733 C2 that boreholes can be viewed visually with an endoscope (borehole endoscopy).

With such endoscopy, the borehole wall is visually inspected on-site; it is not possible to store the observation and a true spatial depiction of the layer data for the rock structure.

OBJECT OF THE INVENTION

The main object of the invention is to provide an apparatus with which it is possible to optically survey the borehole wall of anchor boreholes and to evaluate the information obtained in this manner such that a safety-relevant evaluation of the condition of the rock and objective documentation during driving of the bore are obtained.

SUMMARY OF THE INVENTION

The inventive anchor-borehole probe, which is made as a wireless, i.e. autarchic probe, is moved along the anchor borehole and the surface of the borehole is visually and digitally scanned and stored. This enables documentation of the borehole wall, which can be used to determine the true spatial position of discontinuities and strata by means of an evaluation program. The evaluation program enables uncomplicated administration of the data in a data bank, image processing, and evaluation and interpretation of the borehole images.

The anchor-borehole probe is made explosion-proof for use in underground coal mines.

Travel detection is performed using a contact wheel on which a motion sensor is arranged for determining the travel. It is also possible for the probe movement to be acquired directly with a motion sensor. This motion sensor radiates onto the borehole wall and the reflections during movement of the probe are detected and the travel is determined therefrom.

Using the integrated position sensors, the position of the probe in the borehole is acquired and stored together with the image information. A determination of the true position of the discontinuities is made using the evaluation program and includes the probe spatial position data.

The stored digital image of the surface of the borehole wall is used for structural analysis and for analyzing lithological and petrographical properties.

The true spatial positions of the discontinuities and their frequency distribution are used to determine the fissure bodies in the ends of a path or in the head of a tunnel. The considerable travel into the borehole provides optimized, independent and objectively comparable information on the course and condition of the fracture and condition of the segment head.

Using the evaluation program and the database it is possible to compare data from older inspections with more recent inspection results so that changes in the fracture openings can be detected. This prompt recognition of fracture zones makes it possible to take action early on. It is thus possible to assess the rock structure's condition in terms of safety at any time. In addition, information regarding the rock structure's properties is very important during planning and optimization of the path supports and particularly anchor dimensioning. If there are any problems when driving, the anchor borehole can be documented quickly.

Power is supplied to the anchor-borehole probe using conventional Mignon batteries. The images of the borehole walls are acquired digitally using a color CCD sensor and are stored in the probe. The memory can hold a plurality of measurement operations so that the probe does not have to be read out after each measurement. Monitoring and calibration of the anchor-borehole probe is done by a mobile PC using a high-speed infrared interface integrated into the battery section at the rear end of the probe. The data acquired can also be read out via this infrared interface.

Normally the recordings taken with the anchor-borehole probe are copied out of the probe memory using a USB read-out box and are imported by the software. An assistant supports input of specific additional information for each measurement. Possible additional information includes supplementary comments on the data regarding borehole length and diameter and classification of locations and boreholes, if these have already been defined during earlier measurements.

In addition, there are numerous options for graphics processing of the digital images recorded by the probe. The technician can for instance crop the images; change brightness, contrast, intensity, and gamma value; adjust sharpness; and smooth. The images can be rotated and aligned on their axial orientation. In addition there is a clean-up function for eliminating measurement artifacts.

Using the software, sufficient data for the rock structure that has been bored through can be determined from the borehole images. Determination of the discontinuity orientation is performed semi-automatically by "picking" (clicking on) and classifying the types (e.g., fracture, stratum surface) of the structures that can be seen in the image. The evaluation program can be used for additional processing of the spatial position data for the probe to determine the true spatial positions of the discontinuities. Lithological description of the corresponding depths is also possible.

Rock identification and establishment of limits thus occurs in the framework of the evaluation, as does the determination of the scope and degree of fracture zones. All of the data are stored in the database for documentation and repeat measurements.

The structures are marked both in the image of the borehole wall and in various 3D-views as surfaces. Initially 2D forms are created for individual cross-sections of the path using borehole endoscopy; in addition the software permits a 3D-representation of the boreholes (position in the tunnel/path/bore problem with discontinuity structure).

Using the image data archived and stored in the data base and the information about the borehole (location, spatial position, dimensions, tunnel profile, etc.), it is possible to compare current measurement data to measurements in the same borehole that were taken at an earlier point in time or to data for adjacent boreholes. In this manner it is possible to determine the type, extension, and appearance time of weak zones in the path.

In one preferred embodiment, the anchor-borehole probe is a wireless autarchic optical probe with a diameter of 23 mm. It is thus suitable for digital imaging of the walls of boreholes that have a diameter of 25 to 37 mm. Due to its small diameter and light weight, the probe can be moved manually in the borehole using extension rods.

The borehole probe constitutes a video head, a path sensor, an electronics module, a memory module, and a battery element that also holds an infrared interface. Data transmission makes it possible to monitor inspections.

Imaging is controlled using the path sensor, which in addition to imaging control also provides depth measurement and thus the option for precisely measuring structures, e.g. discontinuity distances and RQD indices, determining crack width, stratum thicknesses, etc.

The true spatial position of the discontinuity structure can be determined using the position sensor values.

BRIEF DESCRIPTION OF THE DRAWING

The invention is described in greater detail in the following using an illustrated embodiment and drawings.

Figure 2:
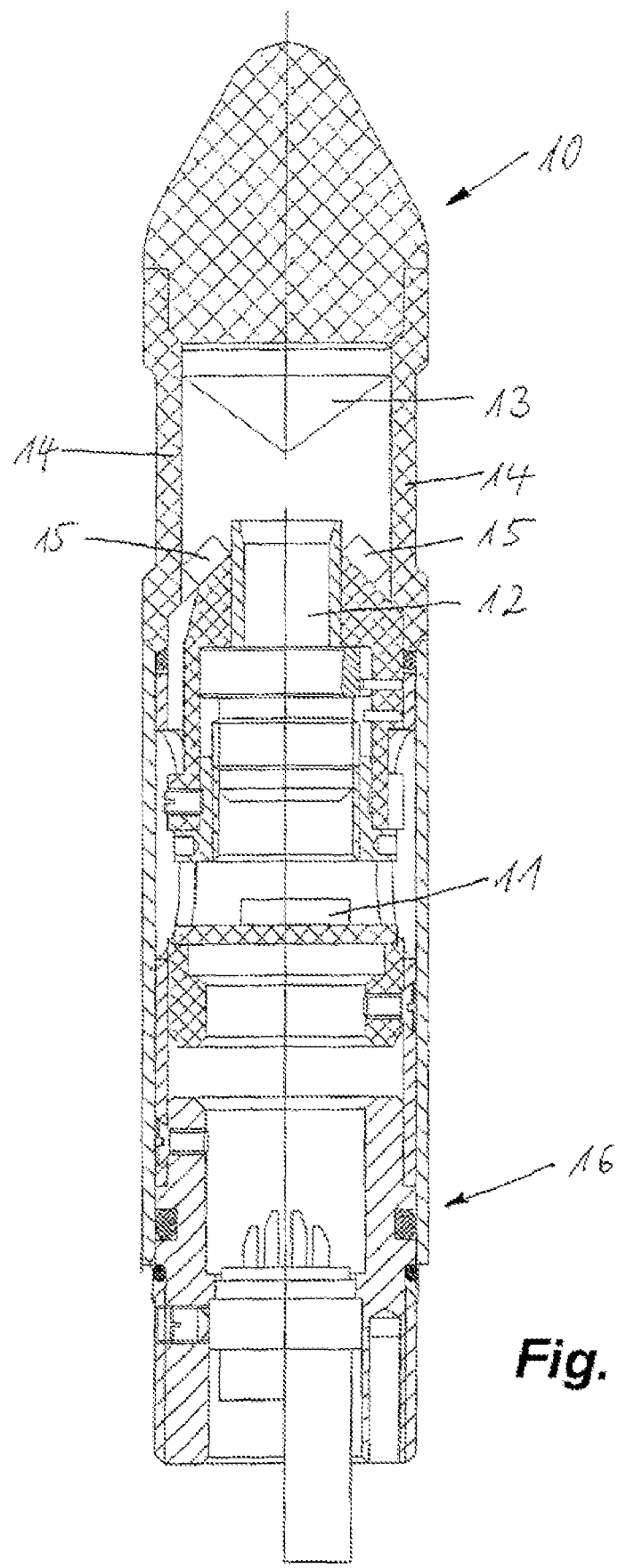
Figure 3:
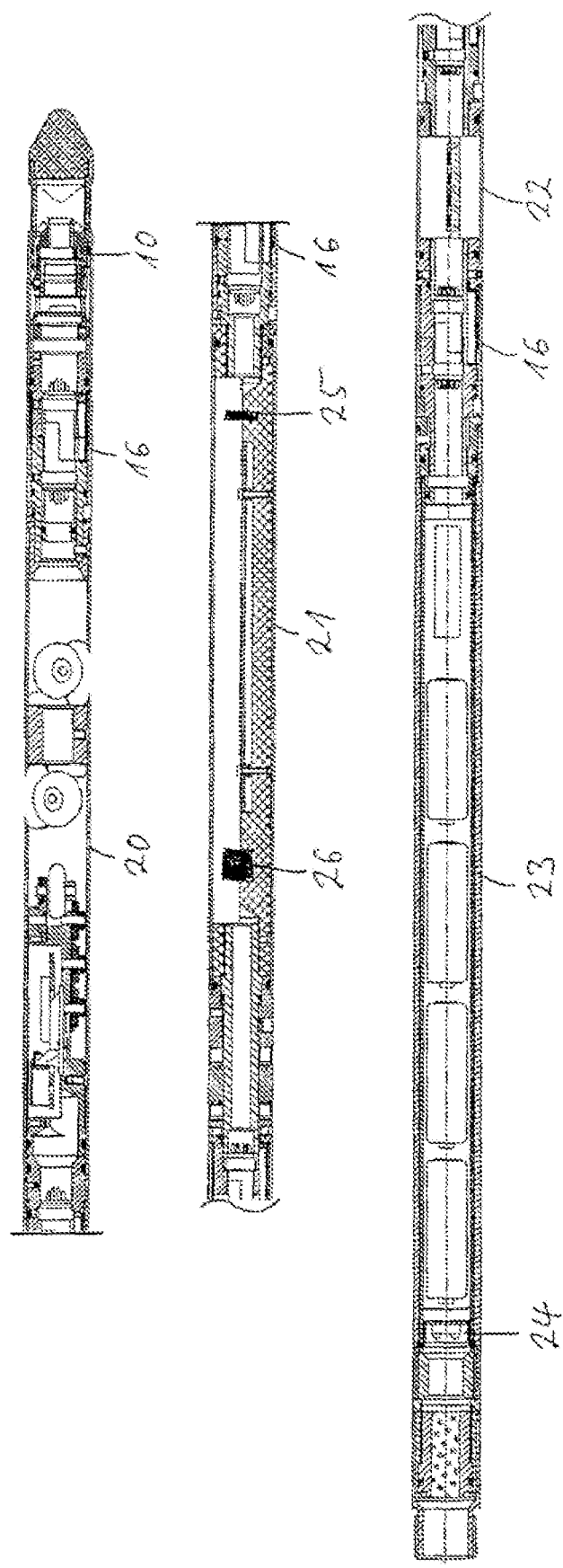
Figure 4:
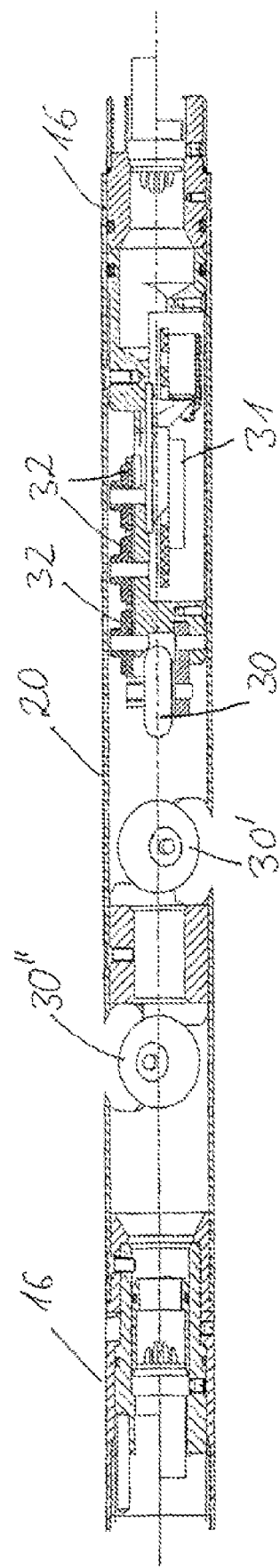

FIG. 1 is a schematic depiction of the method for determining the rock structure in the path lining;

FIG. 2 is a section through the video head;

FIG. 3 is an overall depiction of the anchor-borehole probe;

FIG. 4 is a schematic depiction of the travel sensor; and

Figure 5:
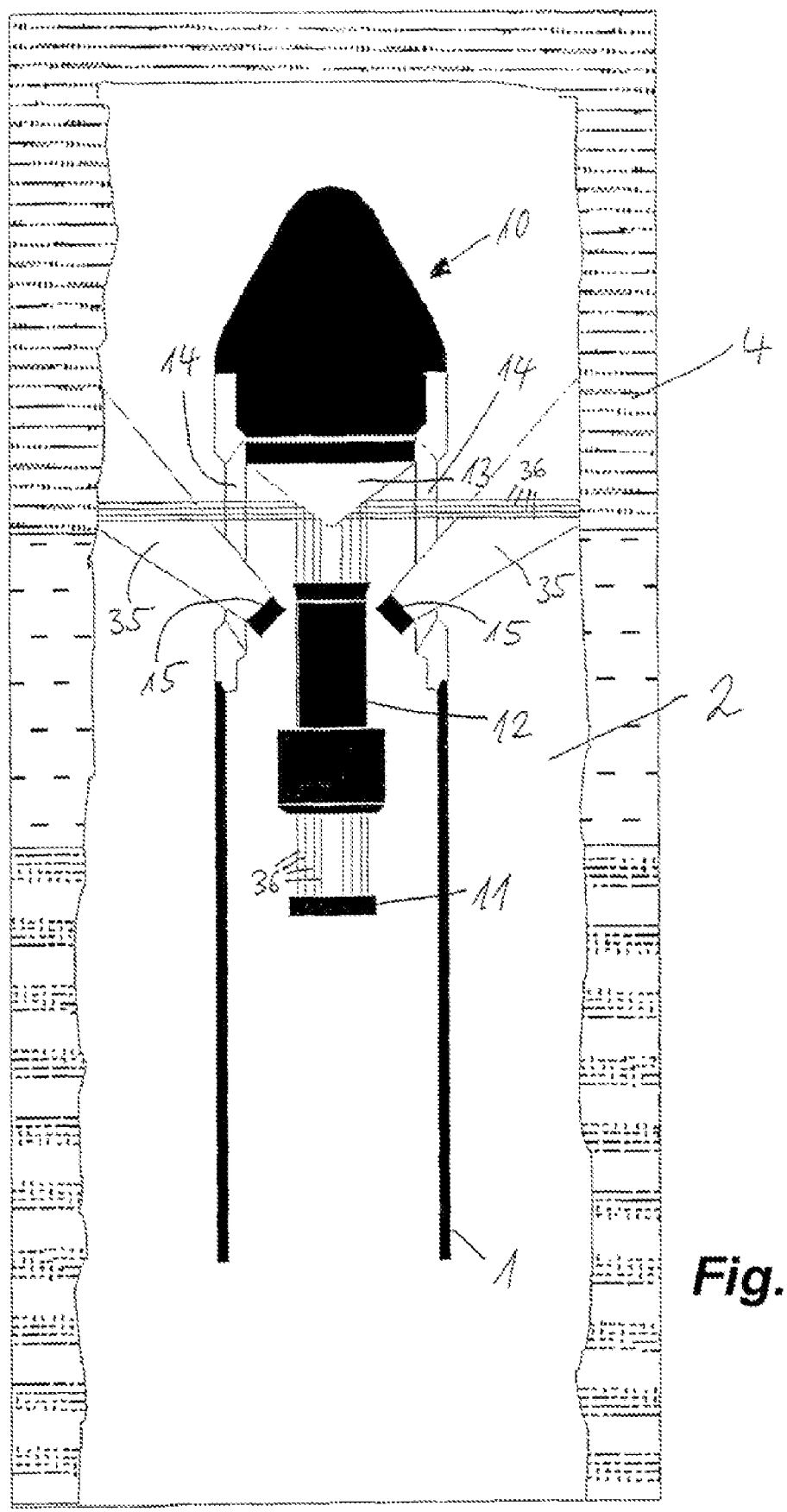

FIG. 5 is a schematic depiction of the video head in a borehole.

SPECIFIC DESCRIPTION AND EXAMPLES

Example

An anchor borehole is inspected with a probe that has the following specifications.

| | |
|---|---|
| Power supply: | 5 × Duracell MN 1500, 1.5 V |
| Data memory: | 256 MB |
| Probe length: | 1,300 mm |
| Probe diameter | 23 mm |
| Probe weight: | 2.2 kg |
| Sensor: | COLOR CCD |
| Measurement cycle: | Max. 25 images per second |
| Measurement speed: | Max. 5 cm per second |
| Illumination: | 8 white light-emitting diodes |
| Depth measurement: | Wheel-driven travel sensor |

The probe is moved along the borehole using a pipe string. Bars built into each coupling ensure good control of the orientation of the probe in the borehole. The anchor-borehole probe scans an angle of 360 degrees, i.e. it covers the entire borehole wall. In the two-dimensional image of the borehole wall surface, which corresponds to a cylinder surface, the borehole wall is shown unrolled. What this leads to is that planar structures, such as e.g. stratum surfaces, fissures, etc. that are not exactly perpendicular to the axis of the borehole appear as sinusoidal lines in this view. The true spatial position and frequency of the fissure surfaces can be detected and illustrated by inspection with the probe.

FIG. 1 provides a schematic representation of the method for inspecting anchor boreholes for determining the rock structure in the path lining. An anchor-borehole probe 1 is moved along an anchor borehole 2 using a pipe string. The bore 3 has additional boreholes 2'. The structure of the rock 4 can be analyzed using the anchor-borehole probe 1. The anchor-borehole probe 1 is positioned in the anchor borehole 2 in the area of a crack 5. The video head is used to digitally record a two-dimensional image 6 of the borehole wall surface.

As can be seen in FIG. 2, a video head 10 has a color CCD sensor 11 that has a lens 12. Using a conical mirror 13, it is possible to optically digitally acquire the borehole wall, which is illuminated by light-emitting diodes 15, through a viewing window 14. A plug connector 16 is provided at the lower end of the video head 10.

FIG. 3 illustrates the anchor-borehole probe 1. It constitutes the video head 10, the travel sensor 20, an electronics module 21, a memory module 22, and a battery section 23 that also contains an infrared interface 24. Two position sensors 25 and 26 are provided in the electronics module 21. The individual constituent parts of the anchor-borehole probe 1 are joined to one another using plug-in connectors 16.

As can be seen from FIG. 4, the travel sensor 20 comprises 3 spring-mounted wheels 30, 30', and 30" that are arranged offset by 120 degrees. A motion sensor 31 is provided on the wheel 30 for determining the travel distance of the anchor-borehole probe 1. Because of space considerations, the movement of the wheel 30 is transmitted to gears 32 and detected by the motion sensor 31.

It can be seen from FIG. 5 that the video head 10 of the anchor-borehole probe 1 is positioned in the anchor borehole 2. The wall of the anchor borehole 2 is illuminated with the light-emitting diodes 15 using a conical beam of light 35. Depending on the travel, the borehole wall of the anchor borehole 2 is visually digitally acquired in the area of the beams 36 using the color CCD sensor 11. This image of the borehole wall is stored using the evaluation program and inspected semi-automatically using a menu control. This is how the structure of the rock 4 is determined.

The invention claimed is:

1. A probe for inspecting an anchor borehole, the probe comprising:
    a video head provided with means including a color CCD sensor, a lens, a conical viewing window, and light emitting diode for illuminating and optically scanning a borehole surface;
    a travel sensor;
    an electronics module including two position sensors;
    a memory module;
    a battery section carrying an infrared interface, the probe being cableless and autarchic; and
    means for securing the battery section to a leading end of a push rod.

2. The anchor-borehole probe defined in claim 1 wherein the travel sensor comprises
- three spring-mounted offset angularly of a longitudinal axis of the probe by about 120° and
- a sensor connected to one of the wheels.

3. The anchor-borehole probe defined in claim 1 wherein the travel sensor is provided with a noncontacting motion sensor.

4. The anchor-borehole probe defined in claim 1 wherein the probe has an explosion-proof housing.

5. The anchor-borehole probe defined in claim 1 wherein the video head is at a leading end of the probe and the battery section and infrared interface are at a trailing end of the probe.

* * * * *